United States Patent [19]
Tiegel

[11] 4,012,947
[45] Mar. 22, 1977

[54] METHOD AND APPARATUS FOR TESTING BATTERY CONNECTOR WELDS

[76] Inventor: Ernest G. Tiegel, Bragato Road, Belmont, Calif. 94002

[22] Filed: Apr. 10, 1974

[21] Appl. No.: 459,568

[52] U.S. Cl. .................................. 73/101; 73/88 B
[51] Int. Cl.² .......................................... G01N 3/24
[58] Field of Search ............................ 73/101, 88 B

[56] References Cited
UNITED STATES PATENTS

| | | | |
|---|---|---|---|
| 2,674,124 | 4/1954 | Barrett | 73/101 |
| 2,959,051 | 11/1960 | Simek et al. | 73/88 B |

Primary Examiner—Richard C. Queisser
Assistant Examiner—Anthony V. Ciarlante
Attorney, Agent, or Firm—Schapp and Hatch

[57] ABSTRACT

A method and apparatus for testing the weld strength of through-the-wall battery connections of the type having upstanding flat plate-like projections on opposite sides of the battery partition the testing being accomplished by application of shear forces to such connections parallel to the partition so that the structural integrity of weldments successfully resisting the test forces is not compromised. The apparatus includes anvil and pressure members which bear against opposite edges of the projections and a pneumatic cylinder formed to urge the anvil and pressure members toward each other parallel to the partition, thus applying a shearing force of desired magnitude controlled by the air pressure supplied to the cylinder.

7 Claims, 4 Drawing Figures

METHOD AND APPARATUS FOR TESTING BATTERY CONNECTOR WELDS

BACKGROUND OF THE INVENTION

The present invention relates to the testing of through-the-wall battery connectors and more particularly to a method and apparatus for testing the structural strength by applying a predetermined force to portions thereof.

Battery plates in lead storage batteries have been connected by various methods. One particularly useful method of which the inventor of the present invention is a joint inventor is disclosed in U.S. Patent application Ser. No. 753,137 filed Aug. 16, 1968 for a Battery Connector for Lead Storage Batteries and Process for Making Same. The method disclosed in that application calls for welding a through-the-wall battery connector formed of upstanding plate projections positioned on opposite sides of a cell partition of a battery. Portions of the projections are pressed into an opening in the cell partition and electrical current is applied to weld them together. The connection is then tested to determine the strength of the weld.

Prior art devices for testing the weld strength of through-the-wall battery connectors usually apply tension tending to pull apart the connectors. Often the flat projections on opposite sides of the wall are not positioned in exact alignment. Such testers typically have one set of jaws which grasps one flat projection on one side of the partition and another set of jaws for grasping the second flat projection on the other side of the wall. When tension is applied to the two flat projections, if they are not in perfect alignment, the jaws will tend to apply force unevenly and deform the cell partition. Moreover, where tension is applied, the malleable lead of the flat projections may give or distort enough to destroy the leakproof integrity of the connector even though the weld is sufficiently strong.

SUMMARY OF THE INVENTION

The general purpose of the present invention is to provide a method and apparatus for testing the weld strength of through-the-wall battery connections of the type having upstanding flat plate-like projections on opposite sides of the battery partition. This is accomplished by applying a shear force to the connections parallel to the partition so that the structural integrity of the weldments that successfully resist the test forces are not comprised.

The apparatus of the present invention includes anvil and pressure members which bear against the edges of the projections. The pressure member is coupled through a piston rod to a pneumatic cylinder which is positioned to apply a force through the pressure member to thereby urge the anvil and pressure members toward each other parallel to the partition. A shearing force is thereby applied to the weldment. A regulator is mounted on the cylinder for regulating the fluid pressure in the cylinder to thereby apply a shearing force of desired magnitude.

Accordingly, an object of the present invention is to provide an apparatus for testing the shear strength of through-the-wall battery connectors.

Another object is to provide means for applying pressure in opposite directions to the two upstanding flat projections of a through-the-wall connector.

A further object of the present invention is to provide pneumatic or hydraulic pressure means for applying the described pressure in a controlled manner, with the force being selectable to an amount sufficient to test the weld without destroying leakproof integrity.

Other objects, advantages and novel features of the present invention will become apparent from the following detailed description of the invention.

BRIEF DESCRIPTION OF THE DRAWINGS

The preferred form of the invention is illustrated in the accompanying drawings, forming a part of this description, in which.

DETAILED DESCRIPTION OF THE PREFERRED EMBODIMENT

Figure 1:
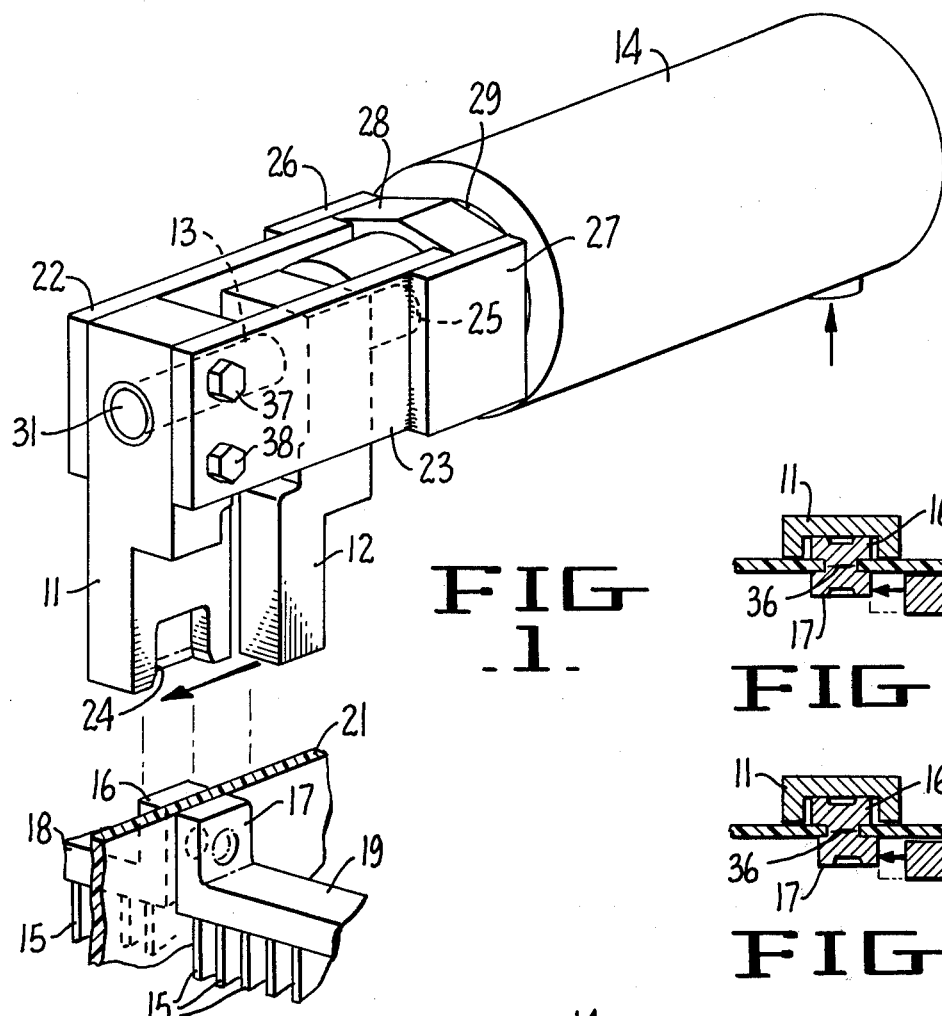
FIG. 1 is a perspective view of an apparatus constructed in accordance with the present invention.
Figure 3:
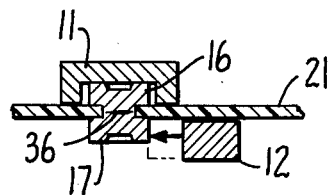
FIG. 3 is a sectional view taken substantially along the plane of line 3—3 of FIG. 2.
Figure 4:
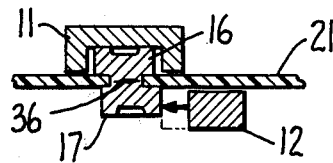
FIG. 4 is a view similar to that of FIG. 3, but showing the anvil and pressure members mounted on a misaligned pair of through-the-wall battery connectors.

Referring to FIG. 1 of the drawings, there is shown an anvil member 11 and a pressure member 12 coupled through a piston rod 13 to cylinder 14 for applying shear force to lugs 16 and 17. The lugs 16 and 17 are connected to battery straps 18 and 19 respectively and are shaped in the form of flat projections. The battery straps 18 and 19 are connected to battery plates 15 as shown. The lugs may be bonded by a weld 36 as shown in FIGS. 3 and 4 through an aperture in the battery cell wall 21 by a suitable method such as disclosed in U.S. Patent application Ser. No. 753,137 filed Aug. 16, 1968 of which the inventor of the present invention is a joint inventor. The method described therein utilizes electrodes formed to press and deform the lead projections to be connected into the aperture. The projections are then spot welded.

The anvil member 11 is secured between plates 22 and 23 by bolts 37 and 38 as shown and may have a pocket 24 formed thereon for grasping the lug 16. Alternatively the anvil member may be formed without a pocket and may be urged against the side of the lug 16 for exerting the shear force thereagainst. The plates 22 and 23 are each welded to support plates 26 and 27 respectively. The support plates are, in turn, welded to a nut 28 which is connected through a neck 29 to the cylinder 14 as shown in FIG. 2.

The pressure member 12 is secured to the piston rod 13 by a suitable fastener means 20 which may be roll pins or screws.

Figure 2:
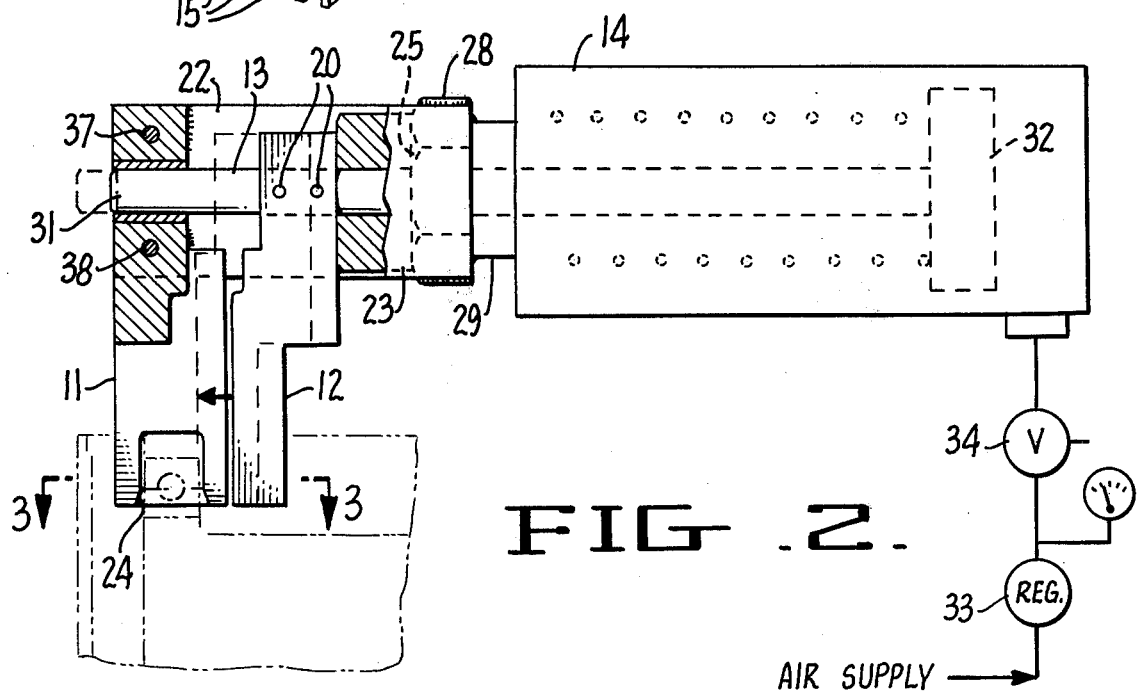
FIG. 2 is a side elevation view of the apparatus of FIG. 1 mounted in operative position on a pair of through-the-wall connectors, with portions of the apparatus being broken away and shown in section.

The piston rod 13 is operative to slide through a sleeve bearing 31 formed on the anvil 11 and an airtight bore 25 in the neck of the cylinder 14, as shown in FIGS. 1 and 2.

The cylinder 14 is preferably a pneumatic cylinder and is adapted to receive air pressure regulated by a regulator 33 and controlled by a valve 34. The valve 34 may have a vent to atmosphere mounted thereon in a manner well known in the art. An air pressure gauge 35 is mounted past the regulator 33 to preset the regulator to the required test shear force.

In the operation of the present invention, the anvil 11 may be mounted on the lug 16 so that the pocket 24 surrounds the lug as shown in FIGS. 3 and 4. The pressure member 12 is urged against the side of the lug 17 as shown in FIGS. 2, 3 and 4 to apply a shear force to the connection of the lugs at a weld 36.

In the preferred embodiment, a pressure in the order of 60 pounds per square inch is generally applied through the air supply to the pneumatic cylinder 14 to determine if the weld 36 can withstand the shear stress. In this embodiment, the cylinder is preferably circular having a diameter in the order of 2½ to 3 inches. Typically satisfactory welds can withstand a shear force extended by 60 pounds per square inch of cylinder pressure. The device may be used to determine the maximum shear force that a weld can withstand by simply increasing the pressure until the weld is sheared. Such welds typically can withstand maximum forces extended by pressure in the cylinder 14 in the order of 80 to 110 pounds per square inch pressure in the air cylinder.

The improvement of the present invention over prior art devices is particularly apparent in testing through-the-wall battery connectors which are not welded in exact alignment.

As shown in FIG. 4, the lugs 16 and 17 formed of flat projections are at times not necessarily in exact alignment when welded through the aperture in the battery cell wall 21. Typical prior art devices which test the weld for tension grasp the lugs 16 and 17 to pull them apart. Such devices cause a torque to be exerted on the lugs which in turn is imparted to the battery cell wall 21 and/or the lugs. The present invention minimizes this torque by applying a shear force through anvil 11 and pressure member 12 so that, if the weld stays together, the lugs and/or partition are not deformed.

Obviously, many modifications and variations of the present invention are possible in the light of the above teachings. For example, the anvil member 11 need not have a pocket 24 formed thereon but instead may be positioned to apply pressure against the side of the lug 16. It is, therefore, to be understood that within the scope of the appended claims the invention may be practiced otherwise than as specifically described.

I claim:

1. A method for non-destructive testing of the weld strength of leak-proof welded through-the-wall battery connections of the type having a pair of upstanding flat plate-like projections on opposite sides of the battery partition with portions deformed into and welded within an opening in the partition, comprising the steps of
   engaging an edge of one of the flat plate-like projections by an anvil member
   engaging an opposite edge of the second of the flat plate-like projections on the opposite side of said battery partition by a pressure member and
   applying pressure to said anvil member and pressure member in opposite directions generally parallel to the partition for testing the weld strength of said connection.

2. The method as described in claim 1 and wherein a preselected amount of pressure is applied to said anvil member and pressure member for effectively testing the weld strength without distorting said projections.

3. The method as described in claim 1 and wherein at least one of the plate projections is prevented from cocking and twisting as said pressure is applied.

4. A device for non-destructive testing of the strength of a leak-proof welded connection between flat battery plate strap lugs positioned against opposite faces of a battery partition and deformed into and electrically fused together within an opening through the partition, comprising
   a pair of members adapted for positioning on opposite sides of the battery partition in close proximity thereto,
   one of said members having a shoulder formed for engaging and bearing against an edge of one lug and the other of said members having a shoulder formed for engaging and bearing against the opposite edge of the other lug whereby relative movement of said members in opposite directions parallel to the faces of the partitions imposes shear force on the leak-proof welded connection without distorting the partition
   frame means mounting said members for said relative movement and
   power means on said frame means connected to said members and formed for urging same in said opposite directions with predetermined force so as to exert a desired amount of shear force on the connection without destroying its leak-proof integrity.

5. A device as described in claim 4 and wherein at least one of said members is formed with a relieved portion defining a pocket formed to fit down over the lug and confine the lug within said relieved portion and the confronting face of the partition for restraining the lug against cocking and pulling away from the partition when said shear force is applied.

6. A device as described in claim 4 and wherein said power means comprises a fluid-operated cylinder adapted for connection to a source of fluid under pressure and a pressure regulating valve communicating with said cylinder and formed for controlling fluid pressure supplied thereto.

7. A device as described in claim 6 and wherein said frame means comprises an elongated body carrying said members for said relative movement, and a piston rod slidable in said body and operatively connected to said fluid-operated cylinder and one of said members.

* * * * *